United States Patent [19]

McAleer et al.

[11] 4,129,646

[45] Dec. 12, 1978

[54] ISOLATING HEPATITIS B DANE PARTICLES

[75] Inventors: William J. McAleer, Ambler; Edward H. Wasmuth, Telford, both of Pa.

[73] Assignee: Merck & Co., Inc., Rahway, N.J.

[21] Appl. No.: 784,191

[22] Filed: Apr. 4, 1977

Related U.S. Application Data

[63] Continuation-in-part of Ser. No. 737,862, Nov. 2, 1976, abandoned.

[51] Int. Cl.² .......................... A61K 39/12; C12K 7/00
[52] U.S. Cl. .......................................... 424/89; 195/1.5
[58] Field of Search .................................. 424/89, 1.5

[56] References Cited

U.S. PATENT DOCUMENTS 4,024,243   5/1977   McAleer et al. ........................ 424/89

OTHER PUBLICATIONS

Fauvel et al. — Can. J. Microbiology, vol. 21 (1975), pp. 905-910.
Tsuda et al. — J. of Immunology, vol. 115, No. 3 (1975), pp. 834-838.
Moritsugu et al. — J. of Immunology, vol. 114 (1975), pp. 1792-1798.
Lipman et al. — J. of Infectious Diseases, vol. 128, No. 5 (Nov. 1973), pp. 664-667.
Gerin — Symposium on Hepatitis Blood Transfusion Proceedings (1972) edited by Vyas et al. — pp. 205-219.

*Primary Examiner*—Sam Rosen
*Attorney, Agent, or Firm*—Donald J. Perrella; Julian S. Levitt

[57] ABSTRACT

Biological fluid containing hepatitis B surface antigen is subjected to isopycnic banding with collection of fractions rich in Dane particles. The Dane particles are useful as diagnostic and immunologic agents.

10 Claims, No Drawings

ISOLATING HEPATITIS B DANE PARTICLES

RELATED APPLICATION

This application is a continuation-in-part of copending application Ser. No. 737,862, filed Nov. 2, 1976 now abandoned.

BACKGROUND OF THE INVENTION

1. Field of the Invention

This invention relates to hepatitis B Dane particles and, more particularly, to a process for preparing hepatitis B Dane particles in high yield and purity.

Hepatitis B is one of the types of viral hepatitis which results in a systemic infection with the principal pathologic changes occurring in the liver. This disease affects mainly adults and is maintained chiefly by transfer of infection from long term carriers of the virus. Usual methods of spread are by blood transfusion, contaminated needles and syringes, through skin breached by cuts or scratches, by unsterilized dental instruments as well as by saliva, veneral contact or exposure to aerosolized infected blood.

The incubation period of type B hepatitis is relatively long: from 6 weeks to 6 months may elapse between infection and the onset of clinical symptoms. The illness usually begins with fatique and anorexia, sometimes accompanied by myalgia and abdominal discomfort. Later jaundice, dark urine, light stools and tender hepatomegaly may appear. In some cases, the onset may be rapid, with appearance of jaundice early in association with fever, chills and leukocytosis. In other cases jaundice may never be recognized and the patient may be aware of a "flu-like" illness. It is estimated that the majority of hepatitis infections result in a mild, anicteric illness.

2. Background of the Invention

Serum obtained from patients with hepatitis B infections contains three distinct morphologic forms which share a common surface antigen ($HB_sAg$) and which can be aggregated with specific antibody directed against $HB_sAg$. The largest of these morphologic forms, a 42-nm to 45-nm double shelled spherical particle, often referred to as the Dane particle (HBV), is believed to be the virus of hepatitis B. The outer surface or envelope of the Dane particle surrounds a 27-nm inner core which does not react with antibody against $HB_s Ag$ and which contains a distinct antigen, the core antigen ($HB_cAg$). Antibody to $HB_cAg$ appears after acute hepatitis B infection, and also can be demonstrated consistently in chronic carriers of $HB_sAg$. Highly sensitive techniques are now available for detection of the $HB_cAg$-Ab system. A deterrent to the more widespread use of such techniques, however, is the absence of a simple yet effective method for obtaining Dane particles from which $HB_cAg$ may be prepared.

3. Objects of the Invention

It is, accordingly, an object of the present invention to provide an improved method for obtaining Dane particles. Another object is to provide a method for concentrating and purifying Dane particles. These and other objects of the present invention will be apparent from the following description.

SUMMARY OF THE INVENTION

Human biological fluid containing $HB_sAg$ is subjected to an isopycnic banding with removal of fractions in the 1.23 – 1.30 g/cc density region. These fractions are rich in Dane particles.

DETAILED DESCRIPTION

The starting material for the purified hepatitis B virus or Dane particle (HBV) of the present invention is fluid containing $HB_sAg$. The fluid may be any human biological fluid containing $HB_sAg$ such as, for example, plasma, saliva, fecal extracts, nasal pharyngeal secretions, bile, spinal fluid, sweat, urine, semen, vaginal secretions or mentrual blood. The most readily obtainable biological fluid in plasma. The plasma is obtained in conventional manner, e.g., by plasmaphoresis. The level of $HB_sAg$ in the human biological fluid may be measured in known manner by any suitable means, e.g., reversed passive hemagglutination or complement fixation. The Dane particles in the resulting fluid are isolated by an isopycnic banding step. When the biological fluid is plasma, it optionally may be cooled and the cryoprecipitate which forms may be removed by light centrifugation before the isopycnic banding step.

In isopycnic banding the partially purified concentrate is contacted with a liquid medium having a density gradient therein which includes the density of the specific antigen being isolated. The liquid medium is then subjected to ultracentrifugation to attain an equilibrium distribution of the serum components through the density gradient according to their individual densities. Successive fractions of the medium are displaced and those containing the desired antigen, i.e. the fractions having a density of from about 1.23 to about 1.30 g/cc, are separated. The concentrations of the solutions forming the gradient are selected so as to encompass the density range of from about 1.0 to about 1.41 g/cc. The liquid medium may be employed in the form of a linear gradient or a step gradient. Preferably it is employed in the form of a step gradient due to its inherent higher capacity for fractionation.

The liquid media used in the isopycnic banding step may be any density gradient in the appropriate ranges. Prior art solutes for such solutions include, e.g. sucrose, potassium bromide, cesium chloride, potassium tartrate and the like. Sodium bromide has not been disclosed heretofore for recovering HBV and is preferred.

The isopycnic banding step is conveniently carried out in a centrifuge, for example, Electronucleonics-K, by filling the stationary rotor with saline solution, then successively displacing the saline solution upwards with aliquots of a liquid medium solution of increasing density until a step gradient is formed. The plasma is introduced at the top of the rotor displacing some of the highest density solution from the bottom. Typically, the volume of plasma is from about 15% to about 40% that of the step gradient. The centrifuge is brought up to speed through a programmed speed control system which prevents mixing during the initial reorientation phase. When equilibrium is attained and the product is in its proper density position, the rotor is slowed down through the same system to prevent mixing upon reorientation to the original configuration. Then the gradient is drained from below and the proper density cut collected.

Due to the small size of the Dane particle, the isopycnic banding step is quite time consuming, requiring about 18 hours of centrifuging. As a result, even operating 24 hours a day, 7 days a week, it is possible to process only about 4 batches per centrifuge per week. Productivity can be increased, of course, by utilizing additional centrifuges. This involves a tremendous capital investment, however, due to the high cost of each centrifuge.

It has now been found that substantial increases in productivity and substantially reduced operating costs are obtained by multiple loading of the isopycnic banding gradient. Multiple loading means subjecting a sample of biological fluid containing HBV to isopycnic banding conditions for a time sufficient to permit substantially all of the HBV in the fluid to pass into the gradient but insufficient to achieve equilibrium, and repeating this step at least once with an additional sample of fluid containing HBV before continuing the isopycnic banding conditions for a time sufficient to achieve equilibrium. If desired, a gradient may be loaded with several, e.g. up to about 6, samples of biological fluid. As the time required for the HBV in the fluid to enter the gradient is only a fraction of that required to reach equilibrium, and as the subsequent time required to reach equilibrium is the same whether the gradient is single or multiply loaded, substantial savings in time and reduction in unit processing costs are obtained.

Alternatively, it has now been found that substantial increases in productivity and substantially reduced operating costs are obtained by treating the biological fluid with a quantity of ammonium sulfate effective to precipitate a protein fraction comprising Dane particles before subjecting the fluid to isopycnic banding conditions. In the case of plasma, generally from about 200 to about 250 g of ammonium sulfate are used per liter of plasma, and preferably about 225 g per liter of plasma. Lesser amounts do not precipitate all of the $HB_sAg$ while greater amounts precipitate additional undesired proteinaceous matter. As a result of this precipitation, the Dane particles from about 20 liters of plasma can be subjected to isopycnic banding in one batch whereas without ammonium sulfate precipitation, only about 1.5 liters of plasma can be subjected to isopycnic banding in a single batch.

After the ammonium sulfate is added, the fluid is agitated to help dissolve the ammonium sulfate. Preferably the fluid is agitated for at least about 3 hours at lowered temperature, preferably at about 5° C., and preferably at least about 4 hours. Additional agitation beyond about 4 hours is not harmful. The precipitate which forms is collected by centrifugation and the pellets resuspended in saline and dialyzed against saline to remove the ammonium sulfate. The resulting fluid concentrate is then subjected to an isopycnic banding using a gradient material having a permissible density range of from about 1.1 to about 1.4 g/cc.

The Dane particle concentrate is found in the density range of from about 1.23 to about 1.30 g/cc.

The Dane particle concentrate may be purified by pelleting through a gradient material such as, for example, sucrose, potassium tartrate, Ficoll or sodium bromide.

While the increased productivity and reduced costs of the ammonium sulfate precipitation technique and of the multiple banding technique of the present invention may be achieved with any suitable gradient, preferably the gradient is sodium bromide.

The isopycnic banding is carried out to equilibrium by centrifuging at from about 40,000 × g to about 80,000 × g for about 10 hours or beyond. It has been found, however, that by centrifuging the fluid for about 4 hours substantially all of the HBV is caused to move into the isopycnic banding gradient. Then the sample of spent fluid is removed and a fresh sample of fluid is layered onto the gradient. Centrifuging may then be continued as previously for about 10 hours or beyond to cause the HBV in both samples to move into the equilibrium density region of the gradient (1.23 to about 1.30 g/cc) to complete the banding. Alternatively the centrifuging may be continued for 4 hours, the spent fluid removed and a third sample of fresh fluid layered onto the gradient. This multiple loading procedure may be repeated six or even more times before completing the banding by centrifuging for about 18 hours.

The ratio of the charge (fluid) volume to the gradient volume may be from about 1:3 to about 1:6. When a single fluid charge is applied to the gradient and centrifuged under isopycnic banding conditions (e.g. for from about 16 to about 20 hours at 30,000 rpms in the KII centrifuge, or for a shorter time at higher speeds or for a longer time at lower speeds) the resulting product generally will have a protein content of approximately 2–5 mg/ml in a volume of b 1.0 liter, depending on the amount of protein in the original plasma.

When a double charge of fluid is applied to the gradient and centrifuged under isopycnic banding conditions, (for from about 16 to about 20 hours at 30,000 rpms, or for a shorter time at higher speeds or for a longer time at lower speeds) the resulting product will have a protein content which is additive for the charges employed, typically in the case of plasma from about 4–10 mg/ml in a volume of 1.0 liter, depending on the amount of protein in the original plasma. The level of protein increases in this manner for each subsequent charge of fluid applied to the gradient.

According to one preferred aspect of the present invention the gradient is formed of sodium bromide. In contrast to heretofore used materials sodium bromide has definite advantages. The solubility of sodium bromide allows the use of high density solutions in the formation of gradients at refrigerator temperatures (2°–6° C.). There are definite economic advantages to using sodium bromide over a salt such as cesium chloride. In a sodium bromide gradient any ions bound to the HBV due to biophysical characteristics will be a sodium salt which is more compatible with many biological systems.

The superior solubility of NaBr at lowered temperatures with respect to KBr permits the use of lowered temperatures more conducive to stability of biological materials. The use of a step gradient rather than a linear gradient is preferred as it accumulates impurities at the step boundaries and permits processing a larger volume of plasma in a single gradient.

The Dane particles may be separated from the NaBr gradient by diluting the gradient with a diluent such as phosphate buffered saline and pelleting the Dane particles. The particles may then be recovered as a concentrate in a suitable medium such as Tris-saline buffer.

The Dane particle concentrate may be further purified by pelleting through a suitable medium such as sucrose containing a proteinaceous stabilizer such as bovine serum albumin (BSA). The resulting pellet may then be resuspended in a suitable medium such as Tris buffer containing a proteinaceous stabilizer such as BSA.

The Dane particle concentrate or the purified Dane particle concentrate may be inactivated by treatment with formalin, absorbed on a physiologically acceptable substrate such as alum, and used as an immunogenic agent.

The following examples illustrate the present invention without, however, limiting the same thereto.

EXAMPLE 1

The rotor of a centrifuge, Electronulceonics K, is filled with 8,400 ml of phosphate buffer. After running the rotor up to 10,000 rpm to degas the system, the following step gradient is pumped into the bottom of the stationary rotor.

1. 2,400 ml of 10% NaBr, $\rho = 1.08$
2. 1,000 ml of 20% NaBr, $\rho = 1.17$
3. 1,500 ml of 30% NaBr, $\rho = 1.28$
4. 3,500 ml of 40% NaBr, $\rho = 1.41$ Plasma containing $HB_sAg$, 1,750 ml, is pumped into the top of the stationary rotor displacing 1,750 ml of 40% NaBr from the bottom of the rotor. The rotor is accelerated to 30,000 rpm and run at this speed for 4 hours. The rotor is then stopped and 1,750 ml of 40% NaBr are pumped into the bottom of the rotor forcing the plasma out the top. An additional 1,750 ml of fresh plasma containing $HB_sAg$ are pumped into the top of the rotor displacing an equal volume of 40% NaBr out the bottom of the rotor. The rotor is then run at 30,000 rpm for 18 hours. After stopping the rotor 1,000 ml of Dane particle rich material in the 1.23 - 1.30 density region is collected.

The (HBV) Dane particles are separated from the NaBr zonal fraction in the following procedure. The zonal fraction (1000 ml) is diluted to 3000 ml using phosphate buffered saline. This material is then placed into 12 type 19 rotor plastic bottles (ea. 250ml/bottle). The material is then centrifuged using a type 19 rotor (Beckman). The rotor is spun at 17,000 rpms (45,000 x g) for 24 hours in order to pellet the Dane particles. The rotor is then stopped and the supernate from each bottle is decanted. The pellet material from all 12 bottles is recovered in a total volume of 5 - 7 ml of Tris-saline buffer. This material is the Dane particle concentrate.

EXAMPLE 2

The Dane particle concentrate is further purified to remove residual traces of antibody protein. One ml of the Dane concentrate of Example 1 is layered over 4 ml of 20% sucrose-1% bovine serum albumin (BSA) in Tris buffer in a SW 65 rotor (Beckman) with $\frac{1}{2} \times 2''$ cellulose nitrate tubes. The particles are centrifuged at 35,000 rpm (125,000 × g) for 4 hours. Post centrifugation, the supernate fluid is decanted and the pellet is gently resuspended in 0.5 ml of Tris buffer with 1% using a cotton tipped swab (premoistened with buffer). The cotton swab is then rinsed with 0.5 ml of buffer. The final volume of Dane particle material is 1 ml. The Dane particles are stored at −70°. C.

EXAMPLE 3

Dane particle concentrate (Type Ad) prepared according to Example 1 is applied to a sodium bromide gradient covering the density range 1.1 to 1.4 g/cm$^3$ and the Dane particles having a bouyant density of 1.23 - 1.30 g/cm$^3$ are separated. This antigen contains about $10^{10}$ of 42-nm Dane particles. The material is treated under aseptic conditions with 1:4000 formalin at 37° C. for 72 hours. Excess formalin is neutralized with sodium bisulfite.

The antigen is then adsorbed on 10% alum [KAl($SO_4)_2 \cdot 12H_2O$] at pH 6.8. A group of guinea pigs is administered intramuscular injections of 3 doses of 0.5 ml at monthly intervals of the antigen adsorbed on alum. The antigen induces circulatory $HB_sAb$ in these animals.

EXAMPLE 4

The procedure of Example 3 is repeated except using type Ay Dane particles and another group of guinea pigs. The antigen induces circulatory $HB_sAb$ in the guinea pigs.

EXAMPLE 5

20 Liters of plasma from hepatitis B donors are clarified by filtration through a 293 mm filter containing an Ap 20 filter membrane (Millipore). Ammonium sulfate, 4.53 kg, is added to the filtrate which is then agitated gently overnight at 5° C. The precipitate which forms is collected by batch centrifugation at 7000 × g for 30 minutes using the JA-10 rotor (3 liter capacity per batch). The pellets post centrifugation are suspended in about 2.25 liters of saline. The concentrated suspension is then dialyzed against 40 liters of saline to remove the ammonium sulfate.

The rotor of a centrifuge, Electronucleonics K, is filled with 8,400 ml of phosphate buffer. After running the rotor up to 10,000 rpm to degas the system, the following step gradient is pumped into the bottom of the stationary rotor:

1. 2,400 ml of 10% NaBr, $\rho = 1.08$
2. 1,000 ml of 20% NaBr, $\rho = 1.17$
3. 1,500 ml of 30% NaBr, $\rho = 1.28$ b 4. 3,500 ml of 40% NaBr, $\rho = 1.41$ The dialyzed suspension from paragraph 1, 2,250 ml, is pumped into the top of the stationary rotor displacing 2,250 ml of 40% NaBr from the bottom of the rotor. The rotor is accelerated to 30,000 rpm and run at this speed for 18 hours. After stopping the rotor, 1,300 ml of Dane particle material in the 1.26 - 1.30 density region is collected. The Dane particles are then separated from the NaBr zonal fractions as described in Example 1 to yield the Dane particle concentrate.

What is claimed is:

1. In a process for concentrating Dane particles from human biological fluid containing $HB_sAg$, the improvement comprising subjecting the fluid to isopycnic banding in sodium bromide density gradient encompassing the density range of from about 1.0 to about 1.41 g/cc and recovering fractions rich in Dane particles within the density range of from about 1.23 to about 1.30 g/cc.

2. A process according to claim 1 wherein the density gradient is a step gradient and the biological fluid is plasma.

3. A process for purifying Dane particles from a human biological fluid comprising subjecting the human biological fluid to isopycnic banding in sodium bromide density gradient and recovering Dane particles from the isopycnic banded fraction having a density region of from about 1.23 g/cc to about 1.30 g/cc.

4. A process for multiple loading a density gradient comprising subjecting a human biological fluid containing Dane particles to isopycnic banding in a density gradient encompassing the density range of from about 1.0 to about 1.41 g/cc under conditions effective to pass substantially all of the HBV in the fluid into the density gradient but ineffective to reach equilibrium, removing the spent fluid, repeating the first step with a fresh sample of fluid at least once and recovering fractions rich in Dane particles within the density range of from about 1.23 to about 1.30 g/cc.

5. A process for isopycnic banding Dane particles from a human biological fluid which comprises multiple loading a density gradient according to claim 4 and then continuing the isopycnic banding under conditions substantially effective to reach equilibrium.

6. The process of claim 5 wherein the density gradient is NaBr and the biological fluid is plasma.

7. A process for concentrating Dane particles from a human biological fluid containing hepatitis B surface antigen comprising precipitating a protein fraction comprising Dane particles by treating the fluid with ammonium sulfate, dialyzing the precipitate,
banding the dialyzed precipitate in a density gradient, and recovering Dane particles from the banded precipitate in the density range of from about 1.23 to about 1.30 g/cc.

8. A process according to claim 7 wherein the density gradient is sodium bromide.

9. A process according to claim 7 wherein the density gradient is a step gradient.

10. A process according to claim 9 wherein the density gradient is sodium bromide.